(12) United States Patent
Hestekin et al.

(10) Patent No.: US 10,987,630 B2
(45) Date of Patent: Apr. 27, 2021

(54) METHOD AND APPARATUS FOR WAFER ENHANCED ELECTRODEIONIZATION OF ACID STREAMS

(71) Applicant: LyondellBasell Acetyls, LLC, Houston, TX (US)

(72) Inventors: Jamie A. Hestekin, Fayetteville, AR (US); Dmytro Demydov, Fayetteville, AR (US); Noel C. Hallinan, Loveland, OH (US); Mure Te, Pearland, TX (US); Barbara Kimmich, Houston, TX (US); Daniel F. White, Houston, TX (US)

(73) Assignee: LyondellBasell Acetyls, LLC, Houston, TX (US)

(*) Notice: Subject to any disclaimer, the term of this patent is extended or adjusted under 35 U.S.C. 154(b) by 87 days.

(21) Appl. No.: 16/288,992

(22) Filed: Feb. 28, 2019

(65) Prior Publication Data

US 2019/0270050 A1    Sep. 5, 2019

Related U.S. Application Data

(60) Provisional application No. 62/637,841, filed on Mar. 2, 2018.

(51) Int. Cl.
*B01D 61/46* (2006.01)
*B01D 61/48* (2006.01)
(Continued)

(52) U.S. Cl.
CPC .......... *B01D 61/485* (2013.01); *B01D 61/46* (2013.01); *B01D 69/02* (2013.01); *C07C 51/47* (2013.01);
(Continued)

(58) Field of Classification Search
CPC ...... B01D 61/485; B01D 61/46; B01D 69/02; B01D 2325/42; B01D 2325/30;
(Continued)

(56) References Cited

U.S. PATENT DOCUMENTS

2010/0133115 A1    6/2010  Gifford
2011/0180477 A1*   7/2011  Ganzi ................. B01D 61/485
                                                        210/638

FOREIGN PATENT DOCUMENTS

CN    102935333 B      12/2014
WO       9820972 A1     5/1998
WO    2008112253 A1     9/2008

OTHER PUBLICATIONS

Huang et al., Application of Electrodialysis to the Production of Organic Acids: State-of-The-Art and Recent Developments, Journal of Membrane Sci., Elsevier BV, NL, vol. 288, No. 1-2, Feb. 3, 2007, pp. 1-12, XP005872372, ISSN:0376-7388, DOI:10.1016/J. MEMSCI. 2006.11.026.
(Continued)

*Primary Examiner* — Arun S Phasge

(57) ABSTRACT

Electrodeionization apparatuses, systems including a reactor system and an electrodeionization system, and methods of purifying acetic acid are provided herein. In some embodiments, the electrodeionization apparatus includes an anode, and three spaced apart membranes located between the anode and the cathode: a first cation exchange membrane, a first anion exchange membrane, a second cation exchange membrane, defining: a first electrode rinse passage between the anode and the first cation exchange membrane, a first concentrate passage between the first cation exchange membrane and the first anion exchange membrane, a feed stream passage located between the first anion exchange membrane and the second cation exchange membrane, and a second electrode rinse passage between the second cation exchange
(Continued)

membrane and the cathode. In some embodiments, the electrodeionization apparatus also includes at least one propionate-selective ion exchange resin wafer within the feed stream passage.

7 Claims, 3 Drawing Sheets

(51) Int. Cl.
      *B01D 69/02*      (2006.01)
      *C07C 51/47*      (2006.01)
      *B01D 71/26*      (2006.01)
      *B01D 71/56*      (2006.01)
      *B01D 71/52*      (2006.01)
      *B01D 71/34*      (2006.01)
      *B01D 71/36*      (2006.01)
      *B01D 71/48*      (2006.01)

(52) U.S. Cl.
     CPC ............. *B01D 71/26* (2013.01); *B01D 71/34* (2013.01); *B01D 71/36* (2013.01); *B01D 71/48* (2013.01); *B01D 71/52* (2013.01); *B01D 71/56* (2013.01); *B01D 2325/30* (2013.01); *B01D 2325/42* (2013.01)

(58) Field of Classification Search
     CPC ........ B01D 71/26; B01D 71/56; B01D 71/52; B01D 71/34; B01D 71/36; B01D 71/48; C07C 51/47
     See application file for complete search history.

(56) References Cited

OTHER PUBLICATIONS

Erhard Hoffmann et al., Recent Advances in Application of Electrodialysis with Bipolar Membranes for Organic Acid Recovery from Fermentation Broth, Current Organic Chemistry, vol. 20, No. 26, Oct. 7, 2016, pp. 2753-2761, XP055592909, NL ISSN:1385-2728, DOI:10.2174/1385272820666160513151103 3.2 Influence of Current Density.
Özgür Arar et al., Various Applications of Electrodeionization (EDI) Method for Water Treatment—A Short Review, Desalination, Elsevier, Amsterdam, NL, vol. 342, Mar. 4, 2014, pp. 16-22, XP028847168, ISSN:0011-9164, DOI:10.1016/J. DESAL.2014.01.028 section 4.3.
The International Search Report and Written Opinion for PCT/US2019/020048 dated Jun. 24, 2019.

* cited by examiner

METHOD AND APPARATUS FOR WAFER ENHANCED ELECTRODEIONIZATION OF ACID STREAMS

CROSS-REFERENCE TO RELATED APPLICATIONS

This application claims the benefit of priority to U.S. Provisional Patent Application No. 62/637,841 filed on Mar. 2, 2018, which is incorporated herein by reference in its entirety.

FIELD OF THE DISCLOSURE

This disclosure relates to separation methods and apparatuses, and more particularly to electrodeionization of liquid streams.

BACKGROUND

Numerous separation methods are known in the art. However, many separation methods, such as distillation and electrodialysis, can be very expensive, particularly when they require a phase change of the material to be separated, such as in distillation. Further, available separation methods are largely unsuitable for separating components in an acidic environment, and are particularly poorly suited for separating organic acids from one another.

Accordingly, improved methods and apparatuses for separating components in acidic environments are needed.

SUMMARY

In one aspect, an electrodeionization apparatus is provided which includes: an anode; a spaced apart cathode; three spaced apart membranes located between the anode and the cathode and comprising a first cation exchange membrane, a first anion exchange membrane, and a second cation exchange membrane defining fluid flow passages therebetween, including: a) a first electrode rinse passage between the anode and the first cation exchange membrane, b) a first concentrate passage between the first cation exchange membrane and the first anion exchange membrane, c) a feed stream passage located between the first anion exchange membrane and the second cation exchange membrane, d) a second electrode rinse passage between the second cation exchange membrane and the cathode; and at least one propionate-selective ion exchange resin wafer located transverse to the fluid flow within the feed stream passage and comprising a macroporous sulfonated or aminated aromatic resin.

In another aspect, a system is provided including: a reactor system configured to produce a product stream comprising acetic acid and propionic acid; an electrodeionization system configured to separate propionic acid from acetic acid, the electrodeionization system including: an anode; a spaced apart cathode; three spaced apart membranes located between the anode and the cathode and comprising a first cation exchange membrane, a first anion exchange membrane, and a second cation exchange membrane defining fluid flow passages therebetween, including: a) a first electrode rinse passage between the anode and the first cation exchange membrane, b) a first concentrate passage between the first cation exchange membrane and the first anion exchange membrane, c) a feed stream passage located between the first anion exchange membrane and the second cation exchange membrane, d) a second electrode rinse passage between the second cation exchange membrane and the cathode; and at least one propionate-selective ion exchange resin wafer located transverse to the fluid flow within the feed stream passage and comprising a macroporous sulfonated or aminated aromatic resin.

In another aspect, a method is provided including the steps of: providing at least one feed stream comprising acetic acid and propionic acid, at least two electrode rinse streams, at least one diluent stream to an electrodeionization system configured to separate propionic acid from acetic acid, the electrodeionization system including: an anode; a spaced apart cathode; three spaced apart membranes located between the anode and the cathode and comprising a first cation exchange membrane, a first anion exchange membrane, and a second cation exchange membrane defining fluid flow passages therebetween, including: a) a first electrode rinse passage between the anode and the first cation exchange membrane, b) a first concentrate passage between the first cation exchange membrane and the first anion exchange membrane, c) a feed stream passage located between the first anion exchange membrane and the second cation exchange membrane, d) a second electrode rinse passage between the second cation exchange membrane and the cathode; and at least one propionate-selective ion exchange resin wafer located transverse to the fluid flow within the feed stream passage and comprising a macroporous sulfonated or aminated aromatic resin; providing an electric potential across the anode and the cathode; and collecting a purified acetic acid stream from the at least one feed stream passage.

BRIEF DESCRIPTION OF THE DRAWINGS

The following figures illustrate embodiments of the subject matter disclosed herein. The claimed subject matter may be understood by reference to the following description taken in conjunction with the accompanying figures, in which like reference numerals identify like elements, and in which:

DETAILED DESCRIPTION

Figure 1:
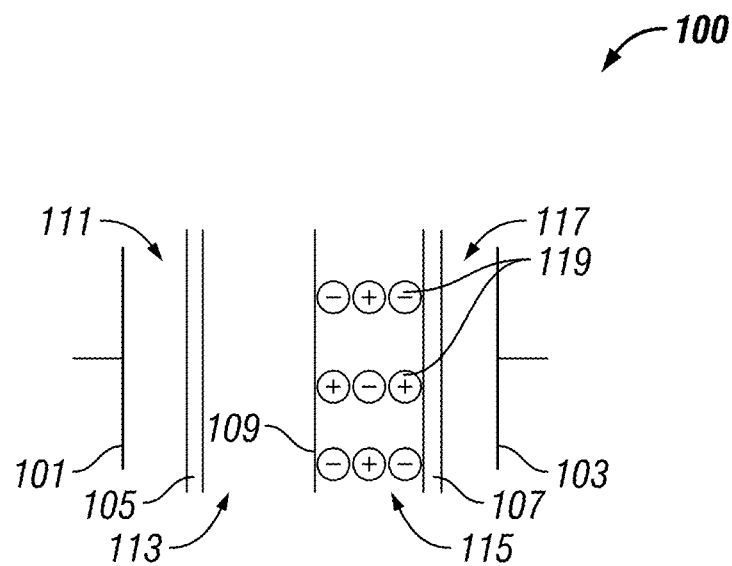
FIG. 1 provides an illustration of a two-compartment electrodeionization system according to an embodiment of the present disclosure.

Unless explicitly stated otherwise in defined circumstances, all percentages, parts, ratios, and like amounts used herein are defined by weight.

Further, in this connection, certain features of the process, apparatus, or system according to this disclosure which are, for clarity, described herein in the context of separate embodiments, may also be provided in combination in a single embodiment. Conversely, various features of the process, apparatus, or system according to this disclosure that are, for brevity, described in the context of a single embodiment, may also be provided separately or in any sub-combination.

When describing a range of dimensions, concentrations, pKas, and the like, it is the Applicant's intent to disclose every individual number that such a range could reasonably encompass, for example, every individual number that has at least one more significant figure than in the disclosed end points of the range. As an example, when referring to a pKa as between 2 and 3, it is intended to disclose that the pKa can be 2, 2.1, 2.2, 2.3, 2.4, 2.5, 2.6, 2.7, 2.8, 2.9, or 3.0, including any subranges or combinations of subranges encompassed in this broader range. Applicant's intent is that these two methods of describing the range are interchangeable. Moreover, when a range of values is disclosed or claimed, Applicant also intends for the disclosure of a range to reflect, and be interchangeable with, disclosing any and all subranges and combinations of sub-ranges encompassed therein. Accordingly, Applicant reserves the right to proviso out or exclude any individual members of any such group, including any sub-ranges or combinations of sub-ranges within the group, or any selection, feature, range, element, or aspect that can be claimed, if for any reason Applicant chooses to claim less than the full measure of the disclosure, for example, to account for a reference that Applicant may be unaware of at the time of the filing of the application. In addition, the ranges set forth herein include their endpoints unless expressly stated otherwise.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, "macroporous" is used broadly to refer to materials having an average pore diameter of from about 10 nm to about 100 microns, for example from about 10 nm to about 5 microns.

In some aspects, apparatuses and methods for separating propionic acid from glacial acetic acid are provided. Glacial acetic acid has low water activity, which typically makes it a poor target for charge-based separation processes. However, electrodeionization methods, systems, and apparatuses for separating propionic acid from acetic acid have surprisingly been found to be effective.

In some aspects, an electrodeionization apparatus is provided which includes an anode, a spaced apart cathode, and three spaced apart membranes between the anode and the cathode. In some embodiments, these membranes include a first cation exchange membrane, a first anion exchange membrane, and a second cation exchange membrane, which each define fluid flow passages between them.

For example, in some embodiments, a first electrode rinse passage is formed between the anode and the first cation exchange membrane. An inert substance, such as water, may flow through the first electrode rinse passage, to assist in removing any buildup from the anode. Similarly, in some embodiments, a second electrode rinse passage is formed between the second cation exchange membrane and the cathode. An inert substance, such as water, may flow through the second electrode rinse passage, to assist in removing any buildup from the cathode.

In some embodiments, a feed stream passage is formed between the first anion exchange membrane and the second cation exchange membrane. In use, a feed stream which includes acetic acid and propionic acid may be transferred to the feed stream passage. In some embodiments, the feed stream is the product stream of a reactor system which is configured to produce a product stream comprising acetic acid and propionic acid. For example, in some embodiments, the reactor system may be used for acetyl manufacturing.

In use, the cation exchange membrane may allow hydroxide to pass from the cathode, through the cation exchange membrane. In use, the anion exchange membrane may allow propionate and acetate ions to pass from the feed stream passage and through the anion exchange membrane.

In some aspects, the feed stream which can be separated by electrodeionization according to this disclosure may include from about 200 ppm to about 100,000 ppm of propionic acid. In some embodiments, the feed stream may include from about 200 ppm to about 1000 ppm of propionic acid, from about 1000 ppm to about 10,000 ppm propionic acid or from about 10,000 ppm to about 100,000 ppm propionic acid, and any ranges therebetween. In some embodiments, the feed stream may have a pKa of from about 2 to about 6, for example, about 2, about 2.5, about 3, about 3.5, about 4, about 4.5, about 5, about 5.5, about 6, or any ranges therebetween. In some embodiments, the feed stream may be entirely non-aqueous.

In some embodiments, one or more propionate-selective ion exchange resin wafers are positioned in the feed stream passage transverse to the fluid flow within the feed stream passage. The one or more propionate-selective ion exchange resin wafers may include a macroporous sulfonated or aminated aromatic resin. In use, the one or more propionate-selective ion exchange resin wafers may promote the selective separation or transfer of propionate ions from the feed stream.

In some embodiments, a purified acetic acid stream can be collected from the at least one feed stream passage. That is, in use, the propionate-selective ion exchange resin wafers and cation and anion exchange membranes function to separate propionate and propionic acid from the feed stream, so that the stream collected from the feed stream passage is a purified acetic acid stream. For example, in some embodiments the purified acetic acid stream can include less than about 500 ppm of propionic acid, for example less than about 500 ppm, less than about 400 ppm, less than about 300 ppm, less than about 200 ppm, less than about 100 ppm, less than about 50 ppm, less than about 20 ppm, less than about 10 ppm, or any ranges therebetween.

In some embodiments, a first concentrate passage is formed between the first cation exchange membrane and the first anion exchange membrane. In some aspects, the electrodeionization apparatus further includes a second anion exchange membrane between the first cation exchange membrane and the first anion exchange membrane, defining a second concentrate passage between the first anion exchange membrane and the second anion exchange membrane.

In some embodiments, one or more acetate-selective ion exchange resin wafers are positioned in the second concentrate stream passage transverse to the fluid flow within the second concentrate passage. The one or more acetate-selective ion exchange resin wafers may include a macroporous sulfonated or aminated aromatic resin. In use, the one or more acetate-selective ion exchange resin wafers may promote the selective separation or transfer of acetate ions from the second concentrate stream passage.

The one or more propionate-selective or acetate-selective ion exchange resin wafers may include Amberlite® IR 120 Na+, a sulfonated aromatic resin, or Amberlyst® A21, an aminated aromatic resin. In some embodiments, the one or more macroporous propionate-selective ion exchange resin wafer further includes a non-ionic aromatic resin or a basic aromatic resin. In some embodiments, the non-ionic aromatic resin may include a cross-linked divinyl-benzene polymer and/or the basic aromatic resin comprises a dialkylamine-modified divinyl-benzene-styrene copolymer. In some embodiments, the non-ionic aromatic resin may include Amberlite® XAD-4, and the basic aromatic resin may include Amberlyst® A-21. The Amberlyst® and Amberlite® materials are available from Rohm & Haas, Philadelphia, Pa.

In some embodiments, the propionate-selective ion exchange resin wafer may have a propionic acid to acetic acid selectivity of from about 10 to about 16. For example, about 10, about 11, about 12, about 13, about 14, about 15, about 16, or any ranges therebetween.

In some embodiments, these membranes are acid-resistant. For example, in some embodiments, one or more of the cation exchange membranes and anion exchange membranes may be stable in a solution of acetic acid for at least 30 minutes, at least 1 hour, at least 2 hours, at least 3 hours, at least 4 hours, at least 5 hours, at least 6 hours, at least 7 hours, at least 8 hours, at least 9 hours, or at least 10 hours. That is, when used in an electrodeionization system as described herein, one or more of the cation exchange membranes and anion exchange membranes may not develop any leaks for at least 30 minutes, at least 1 hour, at least 2 hours, at least 3 hours, at least 4 hours, at least 5 hours, at least 6 hours, at least 7 hours, at least 8 hours, at least 9 hours, or at least 10 hours of electrodeionization.

In some embodiments, the one or more cation exchange membranes and one or more anion exchange membranes may include A7001, Fumasep® FAB, Ralex® AMH-PAD, Ralex® AMH-PES, or any combination thereof. In some embodiments, the one or more cation exchange membranes and one or more anion exchange membranes may include Fumasep® FKM, Fumasep® F930, Fumasep® F-10150-PF, Ralex® CMH-PAD, Ralex® CMH-PES, Ralex® CM-PP, or any combinations thereof. In some embodiments, the one or more anion exchange membrane may include Fumasep® FAM, Fumasep® FAP-450, Fumasep® FAPQ-PP-375, Ralex® AMH-PAD, Ralex® AMH-PES, Ralex® AM-PP, or any combinations thereof. The Fumasep® materials are available from Fumatech BWT GmbH, Bietigheim-Bissingen, Germany. The Ralex® materials are available from Mega A.S., Prague, Czech Republic.

In some embodiments, the one or more anion exchange membranes, and the one or more cation exchange membranes may have a thickness of from about 0.01 to about 1 millimeter, alternatively from about 0.05 mm to about 0.3 mm, from about 0.2 mm to about 0.7 mm. For example about 0.01 mm, about 0.05 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, and any ranges therebetween.

FIG. 1 illustrates a two-compartment electrodeionization apparatus 100 according to an embodiment of the present disclosure. The electrodeionization apparatus 100 includes an anode 101 and a spaced apart cathode 103. The electrodeionization apparatus 100 further includes a first cation exchange membrane 105, a second cation exchange membrane 107, and a first anion exchange membrane 109. The spaced apart membranes 105, 107, and 109 create a first electrode rinse passage 111, a first concentrate passage 113, a feed stream passage 115, and a second electrode rinse passage 117. The feed passage 115 further includes a plurality of propionate-selective ion-exchange resin wafers 119.

In use, a feed stream including acetic acid and propionic acid may be provided to the feed stream passage 115 while an electric potential is created between the anode 101 and cathode 103. Simultaneously, an electrode rinse may be provided to the first and second electrode rinse passages 111, 117, and a stream including propionic acid may be provided to the first concentrate passage 113. The propionate-selective ion-exchange resin wafers 119 promote the creation of propionate (Pr⁻) ions, which then navigate through the first anion exchange membrane 109 out of the feed stream passage 115 and into the first concentrate passage 113. At the same time, these resins may also create some acetate (Ac⁻) ions, which may similarly pass through the first anion exchange membrane 109 out of the feed stream passage 115 and into the first concentrate passage 113. In this way, a purified stream of acetic acid is created in the feed stream passage 115.

Figure 2:
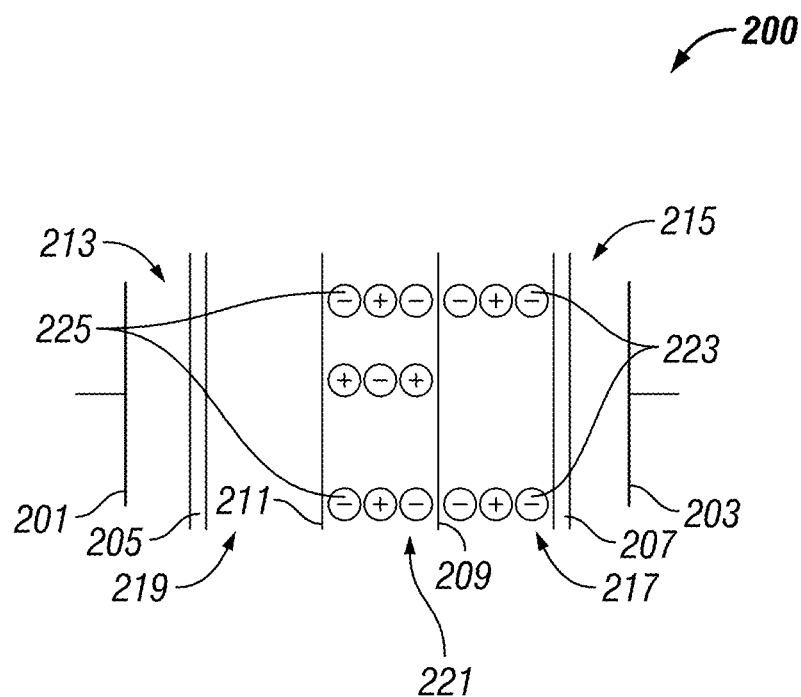
FIG. 2 provides an illustration of a three-compartment electrodeionization system according to an embodiment of the present disclosure.

FIG. 2 illustrates a three-compartment electrodeionization apparatus 200 according to an embodiment of the present disclosure. The electrodeionization apparatus 200 includes an anode 201 and a spaced apart cathode 203. The electrodeionization apparatus 200 further includes a first cation exchange membrane 205, a second cation exchange membrane 207, a first anion exchange membrane 209, and a second anion exchange membrane 211. The spaced apart membranes 205, 207, 209, and 211 create a first electrode rinse passage 213, a second electrode rinse passage 215, a feed stream passage 217, a first a first concentrate passage 219, and a second concentrate passage 221. The feed passage 217 further includes a plurality of propionate-selective ion-exchange resin wafers 223. The second concentrate passage 221 further includes a plurality of acetate-selective ion-exchange resin wafers 225.

In use, a feed stream including acetic acid and propionic acid may be provided to the feed stream passage 217 while an electric potential is created between the anode 201 and cathode 203. Simultaneously, an electrode rinse may be provided to the first and second electrode rinse passages 213, 215, a stream including acetic acid may be provided to the first concentrate passage 219, and a stream including propionic acid may be provided to the second concentrate passage 221. The propionate-selective ion-exchange resin wafers 223 promote the creation of Pr⁻ ions, which then navigate through the first anion exchange membrane 209 out of the feed stream passage 217 and into the second concentrate passage 221. At the same time, these resins may also create some Ac⁻ ions, which may similarly pass through the first anion exchange membrane 209 out of the feed stream passage 217 and into the second concentrate passage 221. In this way, a purified stream of acetic acid is created in the feed stream passage 217. Further, the acetate-selective resin wafers 223 may promote the creation of Ac– ions, which may pass into the first concentrate passage 219. In this way, a stream of dilute acetic acid may be created in the first concentrate passage 219 and a stream of dilute propionic acid may be created in the second concentrate passage 221.

Figure 3:
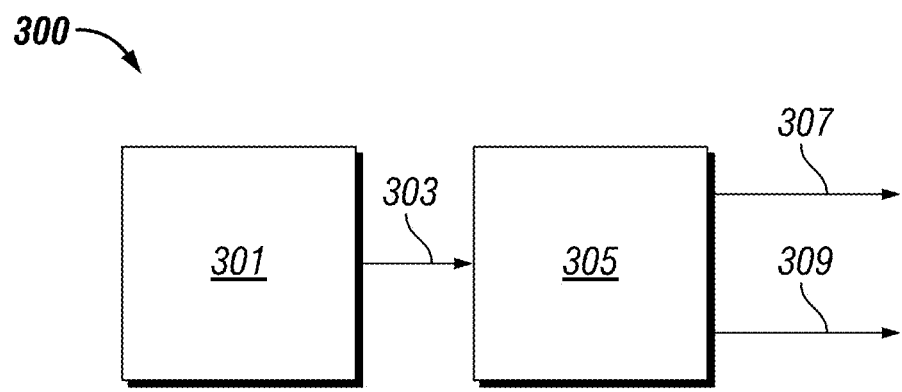
FIG. 3 provides a schematic illustration of a reactor system including an electrodeionization system, according to an embodiment of the present disclosure.

FIG. 3 is a schematic of a system 300 for producing a purified stream of acetic acid. The system 300 includes a reactor system 301 configured to produce a product stream 303 comprising acetic acid and propionic acid. The reactor system 301 may include one or more reactors of any suitable type, and may be configured to produce product stream 303 as an intended product or as a byproduct. The system 300 further includes an electrodeionization system 305 configured to separate propionic acid from acetic acid according to the present disclosure. For example, the electrodeionization system 305 may comprise the electrodeionization apparatuses 100 or 200 discussed above in reference to FIGS. 1 and 2. The electrodeionization system 305 produces a stream of purified propionic acid 307 and an acetic acid stream 309.

EXAMPLES

The present disclosure is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1: Preparing Propionate-Selective Ion-Exchange Resin Wafers

Figure 4:
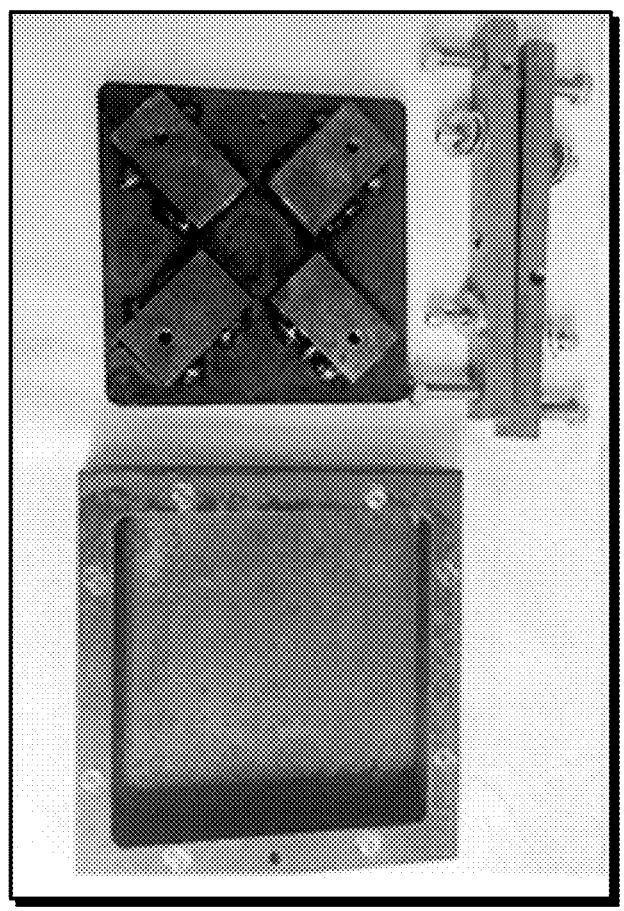
FIG. 4 provides a photograph of a custom cast useful for creating ion-selective resin wafers according to embodiments of the present disclosure.

Mixtures of an anionic exchange resin, a cationic exchange resin, sucrose, and polyethylene were prepared with weight ratios of about 23:23:15:10, placed in a cast and placed in a hydraulic press at a pressure of 10,000 psi at 237° F. for 90 minutes. A custom iron cast was used to prepare the resin wafers. This cast is shown in FIG. 4. Six different wafers were prepared in this cast, as shown in Table 1 below.

TABLE 1

| Wafer No. | Anionic Exchange Resin | Cationic Exchange Resin | Anionic Exchange Resin:Cationic Exchange Resin:Sucrose:Polyethylene Weight Ratio |
| --- | --- | --- | --- |
| 1 | Amberlite ® XAD-4 | Amberlite ® IR-120 Na+ | 1:1:0:0 |
| 2 | Amberlyst ® A-21 | Amberlite ® IR-120 Na+ | 1:1:0:0 |
| 3 | Amberlite ® XAD-4 | Amberlite ® IR-120 Na+ | 23:23:15:10 |
| 4 | Amberlite ® XAD-4 | Amberlite ® IR-120 Na+ | 23:23:17.5:7.5 |
| 5 | Amberlite ® XAD-4 | Amberlite ® IR-120 Na+ | 23:23:20:5 |
| 6 | Amberlyst ® A-21 | Amberlite ® IR-120 Na+ | 23:23:15:10 |
| 7 | Amberlyst ® A-21 | Amberlite ® IR-120 Na+ | 23:23:17.5:17.5 |
| 8 | Amberlyst ® A-21 | Amberlite ® IR-120 Na+ | 23:23:20:5 |

Each of these wafers were first soaked in water for 24 hours. This dissolved the sucrose, for those resins which contained sucrose, making the wafers macroporous. Next, each of these wafers was soaked in acetic acid to activate the wafers.

Example 2: Selective Separation of Propionic Acid in Acetic Acid

Figure 5:
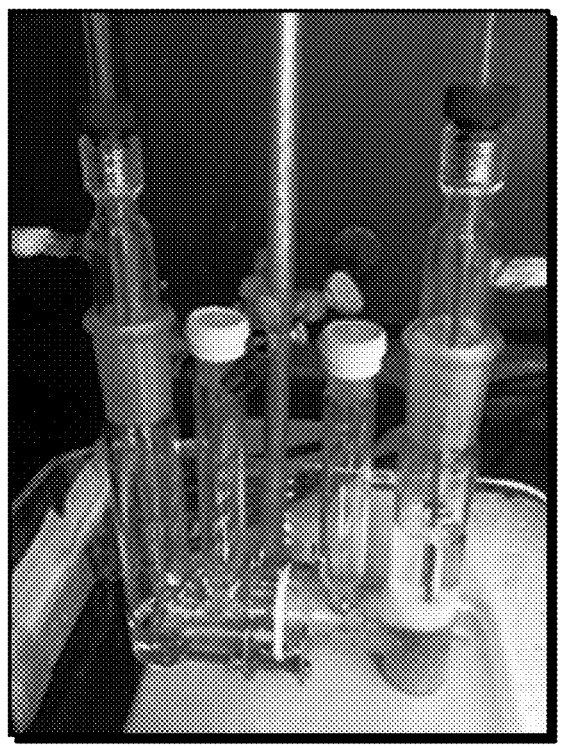
FIG. 5 provides a photograph of a glass electrodeionization system according to an embodiment of the present disclosure.
Figure 6:
FIG. 6 provides a photograph of a micro flow electrodeionization system according to an embodiment of the present disclosure.

Next, several of the wafers prepared in Example 1 were installed into electrodeionization (EDI) cells to test the maximum selectivity of each wafer under various conditions, in a glass EDI cell and a micro flow EDI cell. The glass cell contained about 50 mL of liquid on each side of a membrane and allowed one ion-either hydrogen ions or acetate ions—to pass through. The micro flow cell allowed multiple wafers and multiple membranes, so both hydrogen and acetate ions could be removed. The glass EDI cell is shown in FIG. 5 and the micro flow EDI cell is shown in FIG. 6.

Each of the wafers was placed in an EDI cell between two ion exchange membranes, and a voltage was applied. A feed stream including both propionic acid and acetic acid was provided to the EDI cell, and the maximum selectivity was calculated according to the following formula, wherein $Pr_{in}$ is the initial concentration of propionic acid in the feed stream, $Pr_f$ is the final propionic acid concentration in the product stream, $Ac_{in}$ is the initial concentration of acetic acid in the feed stream, $Ac_f$ is the final acetic acid concentration in the product stream.

$$\frac{\frac{Pr_{in} - Pr_f}{Pr_{in}}}{\frac{Ac_{in} - Ac_f}{Ac_f}}$$

The voltage applied to the EDI cell, the membrane type used, the concentration of the feed stream, and the maximum selectivity are shown in Table 2 below. Samples were collected and analyzed using HPLC, GC, a pH meter, and a conductivity probe meter throughout the experiment.

TABLE 2

| Wafer No. | EDI Voltage | Membrane Type | EDI Cell Type | Feed Stream Concentration | Maximum Selectivity |
| --- | --- | --- | --- | --- | --- |
| 1 | 3 V | Fumasep ® FAS | Glass | 600 ppm propionic acid in acetic acid | 1.7 |
| 2 | 3 V | Fumasep ® FAS | Glass | 600 ppm propionic acid in acetic acid | 1.1 |

TABLE 2-continued

| Wafer No. | EDI Voltage | Membrane Type | EDI Cell Type | Feed Stream Concentration | Maximum Selectivity |
|---|---|---|---|---|---|
| 2 | 3 V | Fumasep ® FAS | Glass | 1:1 weight ratio of propionic acid to acetic acid | 0.5 |
| 2 | 6 V | Fumasep ® FAS | Glass | 1:1 weight ratio of propionic acid to acetic acid | 1.0 |
| 1 | 6 V | Fumasep ® FAS | Glass | 1:1 weight ratio of propionic acid to acetic acid | 1.3 |
| 8 | 6 V | Neosepta ® AMX and CMX | Micro Flow | 600 ppm propionic acid in acetic acid | 15.2 |
| 8 | 6 V | Neoseptag AMX and CMX | Micro Flow | 600 ppm propionic acid in acetic acid | 13.0 |
| 8 | 6 V | Neosepta ® AMX and CMX | Micro Flow | 400 ppm propionic acid and 8 wt. % water in acetic acid | 1.5 |
| 8 | 6 V | A7001 and C7000 | Micro Flow | 400 ppm propionic acid and 8 wt. % water in acetic acid | 1.8 |
| 8 | 6 V | A7001 and C7000 | Micro Flow | 400 ppm propionic acid and 8 wt. % water in acetic acid | 1.7 |
| 8 | 6 V | A7001 and Nafion ® 117 | Micro Flow | 400 ppm propionic acid and 8 wt. % water in acetic acid | 1.4 |
| 5 | 6 V | A7001 and C7000 | Micro Flow | 400 ppm propionic acid and 8 wt. % water in acetic acid | 3.4 |
| 8 | 6 V | Fumasep ® FAB-FKB | Micro Flow | 600 ppm propionic acid in acetic acid | 1.3 |
| 8 | 6 V | Fumasep ® FAB-FKB | Micro Flow | 600 ppm propionic acid in acetic acid | 2.3 |
| 8 | 6 V | Fumasep ® FAB-FKB | Micro Flow | 600 ppm propionic acid in acetic acid | 1.3 |
| 8 | 6 V | Fumasep ® AMH-PAD, CMH-PAD | Micro Flow | 600 ppm propionic acid in acetic acid | 4.6 |
| 8 | 6 V | Fumasep ® AMH-PAD, CMH-PAD | Micro Flow | 600 ppm propionic acid in acetic acid | 1.6 |
| 8 | 6 V | Fumasep ® AMH-PES, CMH-PES | Micro Flow | 600 ppm propionic acid in acetic acid | 3.8 |
| 8 | 6 V | Fumasep ® AMH-PES, CMH-PES | Micro Flow | 600 ppm propionic acid in acetic acid | 4.4 |
| 8 | 6 V | Fumasep ® AMX-FKE | Micro Flow | 600 ppm propionic acid in acetic acid | 3.0 |

During these experiments, it was noted that the acetic acid flow caused significant deformation in the microflow EDI cell for Viton gaskets and swelling of EPDM gaskets. Accordingly, new PTFE gaskets were used for all of the testing. Initially, Neosepta® AMX and CMX membranes were selected and tested for this microflow cell, but after several runs, deformations were noted in these membranes. Similarly, evaluation of Fumasep® membrane performance showed that, while these membranes suffered from less deformation, they were not very acid resistant and, over time, started to leak acid from the dilute stream into the concentrate stream. While not intending to be bound by theory, it is believed that the acid etched microchannels or paths through the membranes, without causing structural damage.

The Neosepta® AMX/CMX membranes showed that in 1 hour, they were able to purify acetic acid, reducing the original propionic acid concentration from 600 ppm to 382 ppm after one hour, and further reducing propionic acid concentration to 345 ppm after four hours. The selectivity over this period of time began at about 5 but was reduced to about 1 by the end of the experiment.

A7001 and C7000 membrane materials were much more acid-resistant, but propionate ion transfer was significantly lower than that achieved with the Neosepta® membranes. The A7001 and C7000 materials are available from Membrane International, Inc., Ringwood, N.J. The Neosepta® materials are available from Astom Corporation, Tokyo, Japan.

Example 3: Acid Resistance of Membranes

In each of the tests described above, the acid-resistance of the membranes was evaluated. The stability or acid-resistance was evaluated by determining the point at which the membrane started physically leaking and the test could not continue. The results of these tests are shown below in Table 3.

TABLE 3

| Membrane | Material | Overall Stability |
|---|---|---|
| Fumasep® FKS | Cation-exchange membrane Homogeneous standard membrane, monofil reinforced (PET, PA, PEEK) | 7 minutes |
| Fumasep® FAS | Anion-exchange membrane Homogeneous standard membrane, monofil reinforced (PET, PA, PEEK) | 2 hours |
| Neosepta® AMX | Anion-exchange membrane Standard grade | 2 hours |
| Neosepta® CMX | Cation-exchange membrane Special resistance grade | 2 hours |
| Neosepta® CMB | Cation-exchange membrane Standard grade | 5 hours |
| Neosepta® AHA | Anion-exchange membrane Special resistance grade | 5 hours |
| C7000 | Cation-exchange membrane ion exchange polymers are then mixed with PVDF resin and heated at high temperature to form sheets Polymer-Ar—$SO_3^-Na^+$ (aryl sulfonic acid sodium salt) | First run 8 hours no cell leak, 2run for 8 hours no leak, some diffusion of acetate ion through membrane |
| A7001 | Anion-exchange membrane ion exchange polymers are then mixed with PVDF resin and heated at high temperature to form sheets Polymer-Ar—$CH_2$—$N^+$—$(CH_3)_3Cl^-$ (quaternary ammonium chloride attached to benzylic portion of styrene/divinylbeneze polymer. | First run 8 hours no cell leak, 2run for 8 hours no leak |
| Nafion® 117 | Cation-exchange membrane available from E.I. DuPont, Wilmington, Delaware. Nafion® 117 membranes are non-reinforced films based on chemically stabilized perfluorosulfonic acid/PTFE copolymer in the acid ($H^+$) form. | First run 5 hours no cell leak, 2run for 5 hours no leak, diffusion of Ac through membrane |
| Fumasep® FAB | Anionic membrane (extremely acid resistant) with excellent chemical and mechanical stability and good selectivity | With Fumasep FKB 3 hours (leak) With Fumasep FKE First run 8 hours no cell leak, 2run for 8 hours no leak |
| Fumasep® FKB | Cationic membrane (electrodialysis applications as separator between feed and acid chamber) with excellent chemical stability, high selectivity, and superior conductivity | 3 hours |
| Fumasep® FKE | Cationic membrane (electrodialysis applications) with excellent chemical stability and good permselectivity | First run 8 hours no cell leak, 2run for 8 hours no leak |

TABLE 3-continued

| Membrane | Material | Overall Stability |
|---|---|---|
| Ralex ® AMH-PAD | Anionic membrane (heterogeneous polyethylene with either polyamide reinforcement) | First run 8 hours no cell leak, 2run for 8 hours no leak |
| Ralex ® AMH-PES | Anionic membrane (heterogeneous polyethylene with either polyamide reinforcement) | First run 8 hours no cell leak, 2run for 8 hours no leak |
| Ralex ® CMH-PAD | Cationic membrane (heterogeneous polyethylene with either polyamide reinforcement) | First run 8 hours no cell leak, 2run for 8 hours no leak |
| Ralex ® CMH-PES | Cationic membrane (heterogeneous polyethylene with either polyamide reinforcement) | First run 8 hours no cell leak, 2run for 8 hours no leak |

Example 4: Alternative Propionate-Selective Ion-Exchange Wafers

As an alternative to the propionate-selective ion-exchange wafers described above, propionate-selective ion-exchange wafers were prepared using polystyrene rather than polyethylene. While not intending to be bound by theory, it is believed that polystyrene is more stable than polyethylene in acidic conditions. Three different wafers were prepared, as shown in Table 4 below:

TABLE 4

| Wafer No. | Anionic Exchange Resin | Cationic Exchange Resin | Polymer | Anionic Exchange Resin:Cationic Exchange Resin:Sucrose:Polymer Weight Ratio |
|---|---|---|---|---|
| 141 | Amberlyst ® A-21 | Amberlite ® IR120 Na+ | Polyethylene | 23:23:15:10 |
| 143 | Amberlyst ® A-21 | Amberlite ® IR120 Na+ | Polyethylene | 23:23:15:10 |
| 173 | Amberlyst ® A-21 | Amberlite ® IR120 Na+ | Polystyrene | 23:23:12.5:12.5 |

These wafers were then inserted into a micro flow cell, as shown in FIG. 6, to evaluate their selectivity and stability. These results are shown in Table 5 below:

TABLE 5

| Wafer No. | Membrane | Selectivity after 1 hour | Selectivity after 3 Hours | Selectivity after 8 hours |
|---|---|---|---|---|
| 141 | Fumasep ® FAM and Fumasep ® FKM | 14.9 | 4.9 | 3.6 |
| 143 | Fumasep ® FAM and Fumasep ® FKM | 5.7 | 3.3 | 1.1 |
| 173 | Fumasep ® FAM and Fumasep ® FKM | 3.1 | 2.1 | 1.5 |

As can be seen from these selectivity tests, the polystyrene wafer (wafer No. 173) is less selective than the polyethylene wafers. However, its selectivity was more stable, suggesting that polystyrene may be more long-lived in these acidic environments than polyethylene. Specifically, after 8 hours wafer no. 141 showed a 76% decrease in selectivity, and wafer no. 143, which was a 6-month-old wafer, showed an 81% decrease in selectivity, while wafer 173—the polystyrene wafer—showed only a 52% decrease in selectivity.

The present disclosure is described above with reference to numerous aspects and embodiments, and specific examples. Equivalents and certain variations of the disclosed embodiments will suggest themselves to those skilled in the art in light of the above detailed description, which are within the intended scope of the appended claims.

What is claimed is:

1. A system comprising:
a reactor system configured to produce a feed stream comprising acetic acid and propionic acid, wherein the feed stream comprises about 200 to 100,000 ppm of propionic acid;
an electrodeionization system fluidly connected to the reactor system, and wherein the electrodeionization is configured to separate propionic acid from acetic acid to produce a product stream, wherein the product stream comprises less than about 500 ppm of propionic acid, the electrodeionization system comprising:
an anode;
a spaced apart cathode;
three spaced apart membranes located between the anode and the cathode and comprising a first cation exchange membrane, a first anion exchange membrane, and a second cation exchange membrane defining fluid flow passages therebetween, the fluid flow passages comprising:
a) a first electrode rinse passage between the anode and the first cation exchange membrane,
b) a first concentrate passage between the first cation exchange membrane and the first anion exchange membrane,
c) a feed stream passage located between the first anion exchange membrane and the second cation exchange membrane,
d) a second electrode rinse passage between the second cation exchange membrane and the cathode; and at least one propionate-selective ion exchange resin wafer located transverse to the fluid flow within the feed stream passage and comprising a macroporous sulfonated or aminated aromatic resin.

2. The system according to claim 1, wherein the propionate-selective ion exchange resin wafer further comprises a non-ionic aromatic resin and/or a basic aromatic resin.

3. The system according to claim 2, wherein the non-ionic aromatic resin comprises a cross-linked divinyl-benzene polymer and/or the basic aromatic resin comprises a dialkylamine-modified divinyl-benzene-styrene copolymer.

4. The system according to claim 1, wherein the propionate-selective ion exchange resin wafer has a propionic acid to acetic acid selectivity of from about 10 to about 16.

5. The system according to claim 1, wherein the feed stream comprises from about 600 to about 5000 ppm of propionic acid.

6. A method comprising:
providing at least one feed stream comprising acetic acid and propionic acid, at least two electrode rinse streams, at least one diluent stream to an electrodeionization system configured to separate propionic acid from acetic acid, wherein the at least one feed stream comprises about 200 to 100,000 ppm of propionic acid, the electrodeionization system comprising:
an anode;
a spaced apart cathode;
three spaced apart membranes located between the anode and the cathode and comprising a first cation exchange membrane, a first anion exchange membrane, and a second cation exchange membrane defining fluid flow passages therebetween, the fluid flow passages comprising:
a) a first electrode rinse passage between the anode and the first cation exchange membrane,
b) a first concentrate passage between the first cation exchange membrane and the first anion exchange membrane,
c) a feed stream passage located between the first anion exchange membrane and the second cation exchange membrane,
d) a second electrode rinse passage between the second cation exchange membrane and the cathode; and
at least one propionate-selective ion exchange resin wafer located transverse to the fluid flow within the feed stream passage and comprising a macroporous sulfonated or aminated aromatic resin;
providing an electric potential across the anode and the cathode; and
collecting a purified acetic acid stream from the at least one feed stream passage, wherein the purified acetic acid stream comprises less than about 500 ppm of propionic acid.

7. The method of claim 6, wherein the purified acetic acid stream comprises less than 400 ppm of propionic acid.

* * * * *